(12) United States Patent
Tamori et al.

(10) Patent No.: US 7,713,627 B2
(45) Date of Patent: May 11, 2010

(54) MAGNETIC PARTICLES COMPRISING AN ORGANIC POLYMER LAYER AND METHOD FOR PRODUCING THE SAME

(75) Inventors: Kouji Tamori, Tsuchiura (JP); Tetsuo Fukuta, Tsuchiura (JP); Satoshi Katayose, Tsukubamirai (JP); Masaru Ueno, Tsukuba (JP); Mitsuhiro Murata, Ushiku (JP)

(73) Assignee: JSR Corporation, Tokyo (JP)

( * ) Notice: Subject to any disclaimer, the term of this patent is extended or adjusted under 35 U.S.C. 154(b) by 283 days.

(21) Appl. No.: 11/688,653

(22) Filed: Mar. 20, 2007

(65) Prior Publication Data

US 2007/0224424 A1    Sep. 27, 2007

(30) Foreign Application Priority Data

Mar. 24, 2006 (JP) ............................. 2006-082614
Jan. 9, 2007 (JP) ............................. 2007-001181

(51) Int. Cl.
    *B32B 5/16* (2006.01)
(52) U.S. Cl. ..................... 428/407; 522/183; 525/451; 525/921
(58) Field of Classification Search ................ 428/403, 428/407; 522/183; 525/451, 921
    See application file for complete search history.

(56) References Cited

U.S. PATENT DOCUMENTS

| 2003/0087284 A1 * | 5/2003 | Sato et al. ................... 435/6 |
| 2003/0175691 A1 | 9/2003 | Elaissari et al. |
| 2006/0223126 A1 * | 10/2006 | Tamori et al. ................ 435/7.5 |
| 2007/0099814 A1 * | 5/2007 | Tamori et al. ............... 510/446 |

FOREIGN PATENT DOCUMENTS

| EP | 1 780 544 | 5/2007 |
| JP | 9-208788 | 8/1997 |
| JP | 10-195099 | 7/1998 |
| JP | 11-174057 | 7/1999 |
| JP | 2000-300283 | 10/2000 |
| JP | 2000-304749 | 11/2000 |
| JP | 2001-158800 | 6/2001 |
| JP | 2001-272406 | 10/2001 |
| JP | 2004-205481 | 7/2004 |
| JP | 2004-331953 | 11/2004 |
| JP | 2005-69926 | 3/2005 |
| JP | 2005-148048 | 6/2005 |
| WO | WO 2004/025297 A1 | 3/2004 |
| WO | WO 2004/040305 A1 | 5/2004 |
| WO | 2006/010083 | 1/2006 |

OTHER PUBLICATIONS

U.S. Appl. No. 11/914,986, filed Nov. 20, 2007, Takahashi, et al.
U.S. Appl. No. 11/961,562, filed Dec. 20, 2007, Tamori, et al.
U.S. Appl. No. 11/954,289, filed Dec. 12, 2007, Tamori, et al.
U.S. Appl. No. 12/529,824, filed Sep. 3, 2009, Katayose, et al.

* cited by examiner

*Primary Examiner*—H. (Holly) T Le
(74) *Attorney, Agent, or Firm*—Oblon, Spivak, McClelland, Maier & Neustadt, L.L.P.

(57) ABSTRACT

Magnetic particles comprising a group shown by the following formula (1):

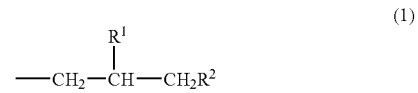

wherein $R^1$ and $R^2$ individually represent a hydroxyl group, a group shown by the following formula (2), or a group shown by the following formula (3), provided that $R^1$ and $R^2$ are not both hydrogen atoms,

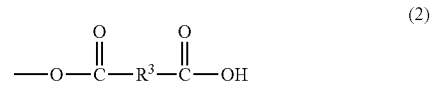

wherein $R^3$ represents an a linear, branched, or cyclic alkylene group having 2 to 6 carbon atoms or an arylene group, and

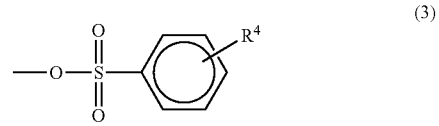

wherein $R^4$ is a hydrogen atom or an alkyl group.

14 Claims, No Drawings

MAGNETIC PARTICLES COMPRISING AN ORGANIC POLYMER LAYER AND METHOD FOR PRODUCING THE SAME

Japanese Patent Application No. 2006-82614 filed on Mar. 24, 2006 and Japanese Patent Application No. 2007-1181 filed on Jan. 9, 2007, are hereby incorporated by reference in their entirety.

BACKGROUND OF THE INVENTION

The present invention relates to magnetic particles exhibiting high sensitivity and low noise when a probe bonded with a biotin is bonded thereto.

Magnetic particles are used as a reaction solid phase of a diagnostic agent using an antigen-antibody reaction in order to detect substances to be examined such as infections, cancer markers, and hormones. In such a diagnostic agent, a probe (primary probe) for inspecting an antibody or an antigen is immobilized on particles. A substance to be inspected in a sample reacts with a second inspection probe after having been caught by the particles via the primary probe. The second inspection probe (secondary probe) is labeled with a fluorescent substance or an enzyme, whereby the target substance is detected by fluorescence or by an enzyme reaction. In recent years, due to a demand for an increase in the inspection sensitivity for early detection of diseases, an increase in sensitivity of a diagnostic agent has been an important subject. In order to increase sensitivity of diagnosis, a method of using enzyme coloring as a detecting means is being replaced by a method of using fluorescence or chemiluminescence, both of which ensure higher sensitivity.

Development of these detection techniques are said to have reached a level in which a one molecule-detection target can be theoretically detected. In practice, however, sensitivity is still insufficient. Generation of noise is given as the cause. Noise is generated by non-specific adsorption of secondary probes and impurities onto the surface of particles. For example, even if a technique that can theoretically detect a one molecule-detection target is used, detection of the one molecule is impossible if several molecules of a secondary probe are non-specifically adsorbed onto the surface of the particles. For this reason, a technique for lowering noise in order to reduce non-specific adsorption of a substance used for inspection onto the particle surface is strongly demanded.

Conventionally, a blocking method has been used for reducing such non-specific adsorption. In the blocking method, after immobilizing a primary probe on the particles, the particle surface is covered with a blocking agent such as albumin or skim milk with minimal adsorptivity of a secondary probe, impurities, and the like. However, some blocking agents may not exhibit a sufficient covering effect. Other blocking agents, which are biological substances, exhibit only poor quality stability. In these cases, even after complete blocking, the blocking effect may reduce over time and non-specific adsorption may occur due to denaturing of the blocking agent and the like. For these reasons, noise reduction by reducing non-specific adsorption has not been sufficiently attained.

In order to solve the problem of non-specific adsorption, a method of introducing a hydrophilic polymer onto the surface of a substrate for immunoassay represented by a 96-well plate has been proposed (JP-A-11-174057, JP-A-2000-304749, and JP-A-2001-272406). However, because the area available for immobilizing a primary probe is limited and the reaction of a primary probe with the target substance to be detected is a solid-liquid reaction, such an immunoassay substrate utilizing a flat surface has problems of poor efficiency of an antigen-antibody reaction, a long period of time required for inspection, and the like.

Furthermore, as countermeasures for decreasing non-specific adsorption, microspheres made from organic polymer particles of a styrene-glycidyl methacrylate copolymer and the like and a physiological active substance bonded to the organic polymer particles via a spacer (JP-A-10-195099, JP-A-2000-300283, WO 04/025297), organic polymer particles with a hydrophilic spacer introduced onto the particle surface (JP-A-2004-331953, WO 04/040305), and the like have been proposed. These organic polymer particles, however, exhibited neither a sufficient effect of reducing noise by reduction of non-specific adsorption nor sufficient immunoassay sensitivity.

The inventors have proposed magnetic particles for immunoassay exhibiting almost no non-specific adsorption, the particles having hydrophilic monomers such as a hydroxyalkyl(meth)acrylate, an alkoxyalkyl(meth)acrylate, a polyoxyalkylene ($C_2$-$C_4$) group-containing (meth)acrylate, an epoxy group-containing (meth)acrylate, and phosphorylcholine-analogous group-containing monomers copolymerized on the surface (JP-A-2005-69926). However, development of particles for immunoassay exhibiting higher sensitivity has been desired.

SUMMARY

An objective of the invention is to provide magnetic particles exhibiting only minimal non-specific adsorption and having high sensitivity and a process for producing the magnetic particles.

In order to achieve the above first object, the inventors have conducted extensive studies and found that non-specific adsorption of biological-related substances such as proteins and nucleic acid on magnetic particles comprising magnetic particles having specific functional groups and a substance having a biotin-bonding site is very small and can reduce noise and that probe-bonded particles exhibiting outstandingly high sensitivity in the field of biochemical and medical products can be obtained by using the magnetic particles. These findings have led to the completion of the invention. The following magnetic particles and methods for producing the magnetic particles can be provided by the invention.

The magnetic particles according to the first embodiment of the invention comprise a group shown by the following formula (1):

wherein $R^1$ and $R^2$ individually represent a hydroxyl group, a group shown by the following formula (2), or a group shown by the following formula (3), provided that $R^1$ and $R^2$ are not both hydroxyl groups,

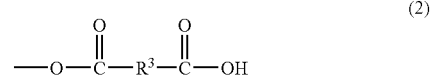

wherein $R^3$ represents a linear, branched, or cyclic alkylene group having 2 to 6 carbon atoms or an arylene group, and

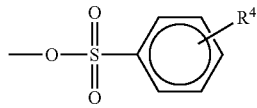
(3)

wherein $R^4$ is a hydrogen atom or an alkyl group.

The magnetic particles may further contain a 2,3-dihydroxypropyl group.

The magnetic particles may also contain an epoxy group.

In addition, the magnetic particles may contain non-magnetic material nuclear particles, a magnetic material layer which covers the non-magnetic material nuclear particles, and an organic polymer layer which covers the magnetic material layer.

In this instance, the organic polymer layer may comprise a first organic polymer layer and a second organic polymer layer which covers the first organic polymer layer. The second organic polymer layer may contain the group shown by the above formula (1). The second polymer layer may comprises a 2,3-dihydroxypropyl group. Furthermore, the second organic polymer layer may contain an epoxy group.

The magnetic particles may have a substance having a biotin-bonding site immobilized thereon. The substance having a biotin-bonding site may be at least one compound selected from the group consisting of avidin, streptavidin, and their derivatives. Furthermore, in this instance, the magnetic particles may contain a biotin-bonded probe bonded thereto.

The method for producing magnetic particles for bonding biotins of the second embodiment comprises introducing a group shown by the above formula (2) into magnetic particles having 2,3-dihydroxypropyl groups and reacting a substance having a biotin-bonding site with the group shown by the above formula (2).

The method for producing magnetic particles for bonding biotins of the third embodiment comprises introducing a group shown by the above formula (3) into magnetic particles having 2,3-dihydroxypropyl groups and reacting a substance having a biotin-bonding site with the group shown by the above formula (3).

In the above method for producing magnetic particles for bonding biotins, the magnetic particles may further comprise an epoxy group and the method further comprises reacting the substance having a biotin-bonding site with the epoxy group.

Magnetic particles for bonding biotins according to the fourth embodiment of the invention have a hydroxyl group originating from a 2,3-dihydroxypropyl group.

"A hydroxyl group originating from a 2,3-dihydroxypropyl group" in the invention refers to either one or both of the two hydroxyl groups possessed by the 2,3-dihydroxypropyl group.

Due to small non-specific adsorption of biochemical-related substances such as proteins and nucleic acids and low noise, the above magnetic particles are suitable as magnetic particles for biochemical inspections exhibiting outstandingly high sensitivity in the field of biochemical and medical products. The above magnetic particles with a biotin-bonded probe bonded thereto exhibit small non-specific adsorption of biochemical-related substances such as proteins and nucleic acids and low noise, exhibit outstandingly high sensitivity in the field of biochemical and medical products, and can provide a high S/N ratio as a biochemical inspection material.

DETAILED DESCRIPTION OF THE EMBODIMENT

The magnetic particles and the method for producing the magnetic particles according to the invention will be described in more detail by way of an embodiment.

1. Magnetic Particles

1.1. Constitution of Magnetic Particles

The magnetic particles (M) of this embodiment comprise a group shown by the following formula (1):

$$—CH_2—\underset{R^1}{CH}—CH_2R^2 \qquad (1)$$

wherein $R^1$ and $R^2$ individually represent a hydroxyl group, a group shown by the following formula (2), or a group shown by the following formula (3), provided that $R^1$ and $R^2$ are not both hydroxyl groups,

(2)

wherein $R^3$ represents an a linear, branched, or cyclic alkylene group having 2 to 6 carbon atoms or an arylene group,

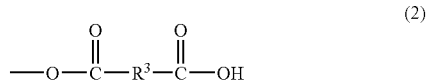
(3)

wherein $R^4$ is a hydrogen atom or an alkyl group.

The magnetic particles (M) of this embodiment can control non-specific adsorption and can bond to a probe due to possession of the group shown by the following formula (1):

Moreover, it is possible to introduce a probe having an amino group, a thiol group, a hydroxyl group, or the like into the magnetic particles (M) of this embodiment by using a coupling reagent, due to possession of the group shown by the above formula (1) in which $R^1$ and $R^2$ are independently a group shown by the formula (2).

As examples of the linear, branched, or cyclic alkylene group having 2 to 6 carbon atoms represented by $R^3$ in the formula (2), groups obtainable by dissociation of hydrogen atoms from an alkyl group such as an ethyl group, an n-propyl group, an isopropyl group, an n-butyl group, a sec-butyl group, a tert-butyl group, a tert-amyl group, an n-pentyl group, an n-hexyl group, an n-octyl group, an n-nonyl group, an n-decyl group, a cyclopropyl group, a cyclobutyl group, a cyclopentyl group, a cyclohexyl group, and a cyclopentylmethyl group can be given. Among these, an ethylene group and 1,2-cyclohexylene group are preferable.

As examples of the arylene group represented by $R^3$ in the above formula (2), arylene groups having 6 to 14 carbon atoms such as a phenylene group, a naphthalendiyl group, a phenanthrendiyl group, and an anthracendiyl group can be given. Of these, a phenylene group and naphthalendiyl group, particularly a 1,2-phenylene group, are preferable.

As $R^4$ in the above formula (3), a hydrogen atom or an alkyl group having 1 to 3 carbon atoms is preferred, specifically at least one selected from a methyl group, an ethyl group, an n-propyl group, and an isopropyl group are preferred. More preferably, the group shown by the above formula (3) is a p-toluenesulfonyloxy group.

The magnetic particles (M) may contain a hydroxyl group originating from a 2,3-dihydroxypropyl group. Specifically, the magnetic particles (M) may contain one of a group of the formula (1) in which one of $R^1$ and $R^2$ is a hydroxyl group and a 2,3-dihydroxypropyl group or both. Such magnetic particles can effectively control non-specific adsorption.

The magnetic particles may further contain an epoxy group.

For example, the magnetic particles (M) in which one of $R^1$ and $R^2$ is a group shown by the above formula (3) and the other is a hydroxyl group and the magnetic particles (M) in which both $R^1$ and $R^2$ are groups shown by the above formula (3) can be prepared according to "the step of introducing a group shown by the formula (3)" of the later described "1.3.1 First Production Method".

For example, the magnetic particles (M) in which one of $R^1$ and $R^2$ is a group shown by the above formula (2) and the other is a hydroxyl group and the magnetic particles (M) in which both $R^1$ and $R^2$ are groups shown by the above formula (2) can be prepared according to "the step of introducing a group shown by the formula (2)" of the later described "1.3.2 Second Production Method".

Either the entirety of the magnetic particles (M) may consist of a polymer part or the magnetic particles (M) may have a core-shell structure, with the shell being formed of a polymer part.

There are no limitations to the magnetic particles (M) insofar as the particles disperse in water and are magnetically separable.

The average particle diameter of the magnetic particles (M) is preferably 0.01 to 10 micrometers, more preferably 0.1 to 8 micrometers, and particularly preferably 0.8 to 5 micrometers. The particle diameter can be determined by a laser diffraction-scattering method. If the particle diameter is less than 0.01 micrometers, it takes a long time for magnetic separation, resulting in insufficient separation of particles from a washing solvent such as water. This makes it difficult to sufficiently remove molecules other than target molecules (e.g. biological-related substances such as proteins and nucleic acids), giving rise to possible inadequate purification. On the other hand, if the particle diameter is more than 10 micrometers, the sensitivity may be impaired as a result of a decrease in the amount of captured biological substances due to a small specific surface area.

The internal composition of magnetic particles (M) may be either homogeneous or heterogeneous. As a structure having a homogeneous internal composition, bulk particles of an inorganic magnetic material of which the outermost surface is treated with a silane coupling agent or the like having 2,3-dihydroxypropyl groups can be given. However, most bulk particles of a homogeneous inorganic magnetic material having a particle size in the above-mentioned preferable range are paramagnetic. If repeatedly separated and refined by magnetism, the magnetic particles may lose their capability of being dispersed in dispersion media. For this reason, the magnetic particles (M) are preferably heterogeneous particles containing fine superparamagnetic particles exhibiting least residual magnetization. Moreover, since magnetic particles (M) with a low specific gravity exhibit retarded precipitation in water which results in easy dispersion in water, magnetic particles containing organic materials are preferable.

The magnetic particles (M) preferably have an internal composition comprising magnetic fine particles with a primary particle size of 50 nm or less and a non-magnetic organic substance, more preferably magnetic fine particles with a primary particle size of 30 nm or less and a non-magnetic organic substance, and most preferably magnetic fine particles with a primary particle size of 20 nm or less and a non-magnetic organic substance. If the magnetic particles (M) contain magnetic fine particles with a primary particle size of more than 50 nm in the internal composition, redispersibility after magnetic separation may be poor.

The internal structure of magnetic particles (M) having a heterogeneous internal composition includes (I) particles comprising a continuous phase of a non-magnetic material such as an organic polymer with fine magnetic material particles being dispersed therein, (II) particles comprising a core of a secondary aggregate of fine magnetic material particles and a shell of non-magnetic material such as an organic polymer, and (III) particles comprising nuclear particles of a non-magnetic material such as an organic polymer (non-magnetic material nuclear particles), a secondary aggregate layer (a magnetic material layer) of superparamagnetic fine particles provided on the surface of the nuclear particles, and an organic polymer layer on the outer layer of the magnetic material layer. Of these, particles (III), which are the magnetic particles having non-magnetic nuclear particles, a magnetic material layer covering the non-magnetic nuclear particles, and an organic polymer layer on the outer layer of the magnetic material layer are preferable. Hereinafter, the nuclear particles covered with a secondary aggregate layer of the superparamagnetic fine particles" are referred to as "mother particles."

The organic polymer used for various particles, specifically the polymer forming the outermost surface of the particles, excluding a core portion of core-shell type particles, must have a hydroxyl group originating from a 2,3-dihydroxypropyl group. The interface between the nuclear particles and the outer layer (a magnetic material layer) and the interface between the magnetic material layer and its outer layer (an organic polymer layer) may be in a state in which the components of both layers are present together.

The above magnetic particles (III) may contain, for example, non-magnetic material nuclear particles, a magnetic material layer which covers the non-magnetic material nuclear particles, and an organic polymer layer which covers the magnetic material layer. In this instance, the organic polymer layer may comprise a first organic polymer layer and a second organic polymer layer which covers the first organic polymer layer. The second organic polymer layer may contain the group shown by the above formula (1). In this instance, the second polymer layer may further contain a 2,3-dihydroxypropyl group. The second polymer layer may further contain an epoxy group.

Providing the first polymer layer to cover nuclear particles having their surfaces covered with a magnetic material layer effectively prevents superparamagnetic fine particles from eluting.

In addition, possession of a 2,3-dihydroxypropyl group by the second polymer layer effectively controls non-specific adsorption. A non-specific adsorptive particle surface is suitable as a surface to bind a probe, for example.

As a preferable method for producing the above-mentioned magnetic particles (I), a method described in JP-A-9-208788 can be given, for example. As a preferable method for producing the above-mentioned magnetic particles (III), a method described in JP-A-2004-205481 can be given, for example.

Although there are no limitations to the composition of the fine magnetic material particles having a primary particle diameter of 50 nm or less, an iron oxide substance typified by ferrite of the formula $MFe_2O_4$ (M=Co, Ni, Mg, Cu, $Li_{0.5}Fe_{0.5}$, etc.), magnetite shown by the formula $Fe_3O_4$, and gamma-$Fe_2O_3$ can be given. Gamma-$Fe_2O_3$ and $Fe_3O_4$ are particularly preferable due to their high saturated magnetization and low residual magnetization. Such fine magnetic material particles having a primary particle diameter of 50 nm or less can be industrially obtained as a magnetic fluid.

As examples of the non-magnetic organic substance, organic low-molecular compounds and organic polymers can be given. As examples of the organic low-molecular compound, a silane coupling agent having 2,3-dihydroxypropyl groups, a chelating agent having 2,3-dihydroxypropyl groups, and a surfactant having 2,3-dihydroxypropyl groups can be given.

As examples of the organic polymer, an addition polymerization polymer having 2,3-dihydroxypropyl groups, and a condensation polymerization polymer having 2,3-dihydroxypropyl groups can be given. A preferable non-magnetic organic substance is an organic polymer having 2,3-dihydroxypropyl groups, preferably an addition polymerization polymer having 2,3-dihydroxypropyl groups, and most preferably a radical polymerization polymer having 2,3-dihydroxypropyl groups.

As examples of a method for producing a radical polymerization polymer having 2,3-dihydroxypropyl groups, a method of (co)polymerizing monomers having 2,3-dihydroxypropyl groups and a method of (co)polymerizing monomers producing a 2,3-dihydroxypropyl group by hydrolysis and hydrolyzing the resulting polymer can be given.

As specific examples of the monomer having 2,3-dihydroxypropyl groups, 2,3-dihydroxypropyl(meth)acrylate and allyl glycerol ether can be given.

As specific examples of the monomer producing a 2,3-dihydroxypropyl group by hydrolysis, a monomer having a 2,3-epoxypropyl group such as glycidyl (meth)acrylate and allyl glycidyl ether; a monomer obtainable by acetalizing a 2,3-dihydroxypropyl group such as 1,3-dioxolane-2-on-4-yl-methyl(meth)acrylate and 1,3-dioxolane-2,2-dimethyl-4-yl-methyl(meth)acrylate; and a monomer obtainable by silylating a 2,3-dihydroxy propyl group such as the di(t-butyl) silylate product of 2,3-dihydroxypropyl(meth)acrylate and 2,3-dihydroxypropyl(meth)acrylate can be given. Although the conditions for hydrolysis vary according to the type of monomer, particles are usually dispersed in water and stirred from several hours to several tens of hours while heating to hydrolyze using an acid, a base, or a fluoride as a catalyst. In the hydrolysis of functional groups originating from monomers, not all of the functional groups of the polymer need to be hydrolyzed as long as storage stability and the like are not hindered. Although the hydrolysis of the functional groups originating from monomers is usually conducted after polymerization of the monomer part, a portion of the functional groups may be hydrolyzed during polymerization.

The copolymerization of a cross-linkable monomer is preferable in order to produce a radical polymerization polymer having 2,3-dihydroxypropyl groups. The cross-linkable monomer refers to a monomer cross-linkable with other monomers containing two or more radically polymerizable unsaturated bonds in one molecule. As specific examples of the cross-linkable monomers, polyfunctional (meth)acrylates such as ethylene glycol diacrylate, ethylene glycol dimethacrylate, trimethylolpropane triacrylate, trimethylolpropane trimethacrylate, pentaerythritol triacrylate, pentaerythritol trimethacrylate, dipentaerythritol hexacrylate, and dipentaerythritol hexamethacrylate; conjugated diolefins such as butadiene and isoprene; divinylbenzene, diallyl phthalate, allyl acrylate, and allyl methacrylate can be given. As further examples of the cross-linkable monomer, hydrophilic monomers such as polyethylene glycol diacrylate, polyethylene glycol dimethacrylate, and poly(meth)acrylates of a polyvinyl alcohol can be given.

Other monomers may further be copolymerized when producing a radical polymerization polymer having 2,3-dihydroxypropyl groups. As other monomers, monomers having a carboxyl group such as acrylic acid, methacrylic acid, maleic acid, and itaconic acid; (meth)acrylates having a hydrophilic functional group such as 2-hydroxyethyl acrylate, 2-hydroxyethyl methacrylate, methoxyethyl acrylate, and methoxyethyl methacrylate; hydrophilic monomers such as acrylamide, methacrylamide, N-methylolacrylamide, N-methylolmethacrylamide, and diacetoneacrylamide; aromatic vinyl monomers such as styrene, alpha-methylstyrene, and styrene halide; vinyl esters such as vinyl acetate and vinyl propionate; unsaturated nitriles such as acrylonitrile; and ethylenically unsaturated alkyl carboxylates such as methyl acrylate, methyl methacrylate, ethyl acrylate, ethyl methacrylate, butyl acrylate, butyl methacrylate, 2-ethylhexyl acrylate, 2-ethylhexyl methacrylate, lauryl acrylate, lauryl methacrylate, stearyl acrylate, stearyl methacrylate, cyclohexyl acrylate, cyclohexyl methacrylate, isobornyl acrylate, and isobornyl methacrylate can be given. As the method for introducing the carboxyl group, a method of copolymerizing an ester monomer having a carboxyl group protected by an alcohol such as tert-butyl(meth)acrylate, 1-methylcyclopentyl (meth)acrylate, 1-ethylcyclopentyl(meth)acrylate, 1-methylcyclohexyl(meth)acrylate, 1-ethylcyclohexyl(meth)acrylate, 2-methyladamantan-2-yl(meth)acrylate, 2-ethyladamantan-2-yl(meth)acrylate, tetrahydrofuranyl(meth)acrylate, and tetrahydropyranyl(meth)acrylate; a cyclic ester monomer such as alpha-acryloyloxy-gamma-butyrolactone, alpha-methacryloyloxy-gamma-butyrolactone, alpha-acryloyloxy-beta, beta-dimethyl-gamma-butyrolactone, alpha-methacryloyloxy-beta,beta-dimethyl-gamma-butyrolactone, alpha-acryloyloxy-alpha-methyl-gamma-butyrolactone, and alpha-methacryloyloxy-alpha-methyl-gamma-butyrolactone; and an acid anhydride such as maleic anhydride and itaconic anhydride, followed by hydrolysis can be used. It is not desirable to copolymerize aromatic vinyl monomers such as styrene, Alpha-methylstyrene, halogenated styrene, and the like, when producing a radical polymerization polymer having 2,3-dihydroxypropyl groups. If these aromatic vinyl monomers are copolymerized, magnetic particles exhibit increased noise.

1.2. Constitution of Magnetic Particles for Bonding Biotins

The magnetic particles for biotin-bonding of this embodiment may have a substance having a biotin-bonding site immobilized on magnetic particles (M). Such magnetic particles for biotin-bonding can be obtained by immobilizing a substance having a biotin-bonding site on magnetic particles (M) having a hydroxyl group originating from a 2,3-dihydroxypropyl group.

As examples of the substance having a biotin-bonding site, avidin, streptavidin, and avidin derivatives such as a cross-linked compound, a modified compound, a complex compound, a denatured compound, and a fragment (hereinafter referred to from time to time as "avidins") can be given.

The magnetic particles for bonding biotins of this embodiment are usually used by dispersing in an appropriate dispersion medium. A dispersion medium which neither dissolves nor swells the magnetic particles is preferably used as the dispersion medium. An aqueous medium can be given as a preferable dispersion medium, for example. The aqueous medium here refers to water or a mixture of water and an organic solvent miscible with water (e.g. alcohols and alkylene glycol derivatives).

The particle diameter of magnetic particles (M) for bonding biotins is preferably 0.03 to 10 micrometers, more preferably 0.1 to 8 micrometers, and most preferably 0.8 to 5 micrometers. The particle diameter can be determined by a laser diffraction-scattering method. If the particle diameter is less than 0.03 micrometers, it takes a long time for magnetic separation, resulting in insufficient separation of particles from a washing solvent such as water. This makes it difficult to sufficiently remove molecules other than target molecules (e.g. biological-related substances such as proteins and nucleic acids), giving rise to possible inadequate purification. On the other hand, if the particle diameter is more than 10 micrometers, the sensitivity may be impaired as a result of a decrease in the amount of captured biological substances due to a small specific surface area.

"Immobilized" herein refers to a state of bonding of a substance having a biotin-bonding site to the extent that the substance may not be removed by washing with a buffer solution commonly used in biochemical experiments. For example, a substance having a biotin-bonding site is regarded to be "immobilized", if 90% or more, more preferably 99% or more, of the substance having a biotin-bonding site remains bonded to magnetic particles after voltex stirring for 15 seconds in a 100 mM phosphate buffer solution, followed by magnetic separation and supernatant replacement. As the method for immobilization, a physical adsorption method such as hydrophobic bonding, and clone bonding and a chemical bonding method such as amide bonding can be given. Chemical bonding is preferred. A preferable method of immobilization by chemical bonding will now be described.

1.3. Method for Producing Magnetic Particles for Bonding Biotins

The magnetic particles for bonding biotins of this embodiment can be prepared by the following first to third production methods, for example.

1.3.1 First Production Method

The first production method may comprise introducing a group shown by the above formula (3) (e.g. a tosyl group) into magnetic particles having 2,3-dihydroxypropyl groups and reacting a substance having a biotin-bonding site with the compound having a group shown by the above formula (3). One or both of the 2,3-dihydroxypropyl groups can be converted into the group shown by the above formula (3) by introducing the group shown by the above formula (3). In this instance, part of the 2,3-dihydroxypropyl groups may remain in the magnetic particles.

When the group shown by the above formula (3) is a tosyl group, magnetic particles (M) having an active group obtainable by tosylating the 2,3-dihydroxypropyl group by introducing the tosyl group is obtained, and a substance having a biotin-bonding site can be immobilized on the magnetic particles (M) by reacting the compound having a biotin-bonding site group with the tosyl group.

In the invention, a "tosyl group" refers to "p-toluenesulfonyl group" and "tosylate" refers to introducing a "p-toluenesulfonyl group", for example, converting a hydroxyl group into a "p-toluenesulfonyl group." The method will be described hereinbelow in the case in which the group shown by the above formula (3) is a tosyl group.

Tosylation can be conducted using a conventional method. For example, tosylation can be achieved by reacting the 2,3-dihydroxypropyl group possessed by the magnetic particles (M) with p-toluenesulfonate in an organic solvent such as pyridine, thereby converting the 2,3-dihydroxypropyl group into a 2-hydroxy-3-(4'-methylphenyl)sulfonyloxypropyl group, a 3-hydroxy-2-(4'-methylphenyl)sulfonyloxypropyl group, or a 2,3-di(4'-methylphenyl)sulfonyloxypropyl group.

Although there are no specific limitations to the p-toluenesulfonate, p-toluenesulfonate chloride can be given as an example. In this procedure, after dispersing the magnetic particles (M) in an organic solvent such as pyridine, p-toluenesulfonic acid chloride is added in an amount from 1 to 50 parts by weight for 100 parts by weight of the magnetic particles (M) and reacted at room temperature for 1 hour to 6 hours. Alternatively, the tosylation may be conducted by condensing the 2,3-dihydroxypropyl group of the magnetic particles (M) and p-toluenesulfonic acid by dehydration to convert the 2,3-dihydroxypropyl group into a 2-hydroxy-3-(4'-methylphenyl)sulfonyloxypropyl group. The reactive group obtained by tosylating a 2,3-dihydroxypropyl group is, for example, a group in which one or both hydroxyl groups of a 2,3-dihydroxypropyl group are tosylated, with specific examples including a 2-hydroxy-3-(4'-methylphenyl)sulfonyloxypropyl group, a 3-hydroxy-2-(4'-methylphenyl)sulfonyloxypropyl group, and a 2,3-di(4'-methylphenyl)sulfonyloxypropyl group.

The magnetic particles for bonding biotins of this embodiment may contain a 2,3-dihydroxypropyl group that has not been tosylated. Specifically, when the magnetic particles for bonding biotins are obtained by the first production method, "a hydroxyl group originating from a 2,3-dihydroxypropyl group" refers to the two hydroxyl groups possessed by the 2,3-dihydroxypropyl group if neither of the two hydroxyl groups is tosylated or the hydroxyl group not tosylated if one of the two hydroxyl groups is tosylated.

After bonding a substance having a biotin-bonding site, the excess amount of the substance having a biotin-bonding site is washed out, thereby obtaining magnetic particles exhibiting outstandingly high sensitivity and low noise due to 2,3-hydroxypropyl groups remaining after deactivating the unreacted tosyl groups. This effect is not expressed by particles having only a group obtained by tosylating a monohydroxypropyl group, for example, by particles possessing only a 3-(4'-methylphenyl)sulfonyloxypropyl group.

1.3.2 Second Production Method (Method of Bonding with a Carboxyl Group)

The second production method may comprise introducing a group shown by the above formula (2) (e.g. a carboxyethylcarbonyloxy group) into magnetic particles having 2,3-dihydroxypropyl groups and reacting a substance having a biotin-bonding site with the compound having a group shown by the above formula (2). One or both of the 2,3-dihydroxypropyl groups can be converted into the group shown by the above formula (2) by introducing the group shown by the above formula (2). In this instance, part of the 2,3-dihydroxypropyl groups may remain in the magnetic particles.

The procedure of introducing the group shown by the above formula (2) can be accomplished by, for example, reacting a 2,3-dihydroxypropyl group with a compound shown by the following formula (4) (dicarboxylic acid anhydride).

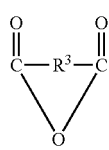

(4)

wherein $R^3$ represents a linear, branched, or cyclic alkylene group having 2 to 6 carbon atoms or an aryl group.

When the group shown by the above formula (2) is a carboxyethylcarbonyloxy group, for example, succinic acid anhydride (n=2 in the above formula (2)) is used as a compound shown by the above formula (4). More specifically, a carboxyl group is introduced into the magnetic particles (M) by introducing a carboxyethylcarbonyloxy group by reacting the succinic acid anhydride with the 2,3-dihydroxypropyl group in the magnetic particles, then a compound having a biotin-bonding site is immobilized on the magnetic particles (M) by reacting the carboxyl group with a compound having a biotin-bonding site.

In the magnetic particles (M), the carboxyl group is a factor for accelerating bonding of biotins by known activation by means of esterification or amidation using a dehydration-condensing agent of water-soluble carbodiimide or the like.

When the magnetic particles (M) have a carboxyl group, avidins can be immobilized onto the magnetic particles (M) by forming an amide bond by the reaction of the carboxyl group with an amino group in the avidins in the presence of the dehydration-condensing agent of water-soluble carbodiimide or the like. In this method, it is possible to previously react the dehydration-condensing agent with the carboxyl group of the magnetic particles (M) and then react avidins with the reactant. Known methods described in JP-A-2001-158800, for example, can be followed for detailed procedures.

1.3.3 Third Production Method (Method of Bonding with an Epoxy Group)

The third production method is the same as the first and second productions methods, except that the magnetic particles (M) may further comprise an epoxy group, and the method further comprises reacting the substance having a biotin-bonding site with the epoxy group.

When the magnetic particles (M) have an epoxy group, avidins (a substance which has a biotin-bonding site) can be immobilized onto the surface of the magnetic particles (M) by forming an amide bond by the reaction of the epoxy group with an amino group in the avidins in an aqueous solvent and an organic solvent. This method is useful due to the capability of chemically bonding avidins to the magnetic particles (M) without requiring an activator or the like.

2. Probe-Bonded Particles and Use Thereof

Due to the capability of immobilizing avidins on the surface, the particles for bonding biotins according to this embodiment can surely combine with a probe to which biotin or a biotin derivative (herein collectively referred to as "biotins") is bonded, such as a nucleic acid and protein.

The probe-bonded particles of this embodiment are magnetic particles for bonding biotins to which a probe to which biotins are bonded (biotin bonding probe) is bonded. Such probe-bonded particles are useful as a diagnostic carrier, bacteria separating carrier, cell separating carrier, nucleic acid separation-purification carrier, protein separation-purification carrier, immobilized enzyme carrier, drug delivery medium, and the like.

As one example of the probe-bonded particles of this embodiment, magnetic particles with an oligonucleotide to which biotins are bonded immobilized on the surface via avidins can be given. Specifically, in this case, the substance having a biotin-bonding site is an oligonucleotide to which biotins are bonded. The length of the oligonucleotide immobilized is from 10 to 1,000 bases, and preferably from 70 to 200 bases. The oligonucleotide immobilized may be a single-stranded DNA, a double-stranded DNA, or an RNA. Such a nucleic acid can be prepared using a commercially-available nucleic acid synthesizer. Such particles with a nucleic acid immobilized thereon can be used generally in genetic engineering such as gene diagnosis. Specifically, it is possible, for example, to directly recover an mRNA from a cell lysate by using the above-mentioned nucleic acid-immobilized particles to which an oligo dT is bound.

As another example of the probe-bonded particles of this embodiment, magnetic particles with a protein to which biotins are bonded (a biotin-bonded protein) immobilized on the surface via avidins can be given. As the protein, an antigen or an antibody is preferable. Any antigens and antibodies reactive with a component generally contained in samples can be used without specific limitations. Examples which can be given include, but are not limited to antigens or antibodies for clotting-fibrinolytic-related inspections such as an anti-antiplasmin antibody for antiplasmin inspection, an anti-D dimer antibody for D-dimer inspection, an anti-FDP antibody for FDP inspection, an anti-tPA antibody for tPA inspection, an anti-thrombin=antithrombin complex antibody for TAT inspection, and an anti-FPA antibody for FPA inspection; antigens or antibodies for tumor-related inspections such as an anti-BFP antibody for BFP inspection, an anti-CEA antibody for CEA inspection, an anti-AFP antibody for AFP inspection, an anti-ferritin antibody for ferritin inspection, and an anti-CA19-9 antibody for CA19-9 inspection; antigens and antibodies for serum protein-related inspections such as an anti-apolipoprotein antibody for apolipoprotein inspection, an anti-beta2-microglobulin for beta2-microglobulin inspection, an anti-alpha1-microglobulin for alpha1-microglobulin inspection, an anti-immunoglobulin antibody for immunoglobulin inspection, and an anti-CRP antibody for CRP inspection; antigens and antibodies for endocrine-function inspection such as an anti-HCG antibody for HCG inspection; antigens and antibodies for infection-related inspections such as an anti-HBs antibody for HBs antigen inspection, an HBs antigen for HBs antibody inspection, an HCV antigen for HCV antibody inspection, an HIV-1 antigen for HIV-1 antibodies, an HIV-2 antigen for HIV-2 antibody inspection, an HTLV-1 antigen for HTLV-1 inspection, a mycoplasma antigen for mycoplasma infection inspection, a toxoplasma antigen for toxoplasma inspection, and a streptolysin O-antigen for ASO inspection; antigens and antibodies for autoimmune-related inspections such as a DNA antigen for anti-DNA antibody inspection, and a heat-denatured human IgG for RF inspection; and antigens and antibodies for drug analysis such as an anti-digoxin antibody for digoxin inspection and an anti-lidocaine antibody for lidocaine inspection. As the antibody, either polyclonal antibodies or monoclonal antibodies may be used.

As more specific examples of use of the probe-bonded particles, quantitative and qualitative analysis comprising bonding an antigen or antibody as a probe to detect a turbidity change of a solution caused by passive agglutination based on an antigen-antibody reaction with the antibody or antigen to be analyzed; collection and concentration of viruses, bacteria, cells, hormones, chemical compounds such as dioxines (as antigens) comprising bonding an antibody as a probe and bonding the antigens to the antibody; and use of the above magnetic particles for bonding biotins as a carrier for enzyme immunoassay utilizing colorimetry or chemiluminescence by bonding an antigen or antibody as a probe can be given. Conventional diagnostic items in which a 96-well plate or the like is used as a carrier can be replaced by an automatic analyzer if the magnetic particles for bonding biotins are used.

In the probe-bonded particles of this embodiment, the substances to be inspected are biological-related substances, chemical compounds, and living organisms which are contained in immunoassay reagents and inspection samples. In the invention, the term "biological-related substance" refers to all substances relating to biological bodies. As examples of the biological-related substance, substances contained in biological bodies, substances derived from substances contained in biological bodies, and substances which can be used in biological bodies can be given.

For example, the biological-related substances to be detected include, but are not limited to, proteins (e.g., enzymes, antibodies, aptamers, and acceptors), peptides (e.g., glutathione), nucleic acids (e.g., DNA and RNA), carbohydrates, lipids, and other cells and substances (e.g., various blood-originating substances containing various blood cells such as platelets, erythrocytes, and leukocytes); hormones (e.g., luteinizing hormones and thyroid stimulating hormones); and proteins and nucleic acids which are components of viruses, bacteria, fungi, protozoan, and parasites). As more specific examples of the proteins, proteins of biological origin and proteins used as a cancer marker such as a prostate gland unique marker and a bladder cancer marker can be given.

There are no specific limitations to the chemical substances to be detected. For example, environmental pollutants such as dioxins and medical supplies (for example, antibiotics, anticancers, and antiepileptic drugs) can be given.

There are no specific limitations to the target biological substances to be detected. For example, various cancer cells, various floating cells, viruses (for example, hepatitis B virus, hepatitis C virus, simple herpes virus, and HIV), bacteria (for example, Neisseria gonorrhoeae, MRSA, and Escherichia coli), fungi (for example, Candida, Cryptococcus, Aspergillus), protozoan, parasites (for example, toxoplasma and malaria), and the like can be given.

As an example of the method for producing the probe-bonded particles, a method of bonding particles for bonding biotins to a probe to which biotins are bonded (a biotin-bonded probe) by applying a known method for bonding biotins to avidins can be given.

For example, a probe-bonded particles on which a protein or oligonucleotide is immobilized can be prepared by mixing the above-mentioned biotin-bonded particles with a protein or oligonucleotide modified by a biotin (a biotin-bonded probe) at room temperature for 10 minutes to one hour in a phosphate buffer or a 1 M sodium chloride-containing phosphate buffer, and removing unreacted protein or oligonucleotide by solid-liquid separation. It is needless to mention that biotins can be bonded to avidins which are immobilized on the surface of the biotin-bonded particles by this method.

As the biotin derivative, biotin-epsilon-N-lysine, biocytin-hydrazide, 2-iminobiotin, amino or sulhydril derivatives of biotinyl-epsilon-N-aminocaproic acid-N-hydroxysuccinimide ester, sulfosuccinimide iminodiotin, biotin bromoacetyl-hydrazide, p-diazobenzoylbiotin, and 3-(N-maleinimidepropionyl)biotin can be used, for example.

As examples of the method for modifying a protein or oligonucleotide with biotins, (i) a method of reacting an ester of a biotin and an N-hydroxyamide (e.g. biotin-N-hydroxysuccinimide) with an amino group of a protein molecule to modify the protein with the biotin, and (ii) a method of bonding phthalimide triethylene glycol to the 5'-terminal of an oligonucleotide and hydrolyzing the reaction product with ammonium hydroxide to form a primary amino group, and bonding biotin-N-hydroxysuccinimide, for example, to the amino group, thereby modifying the 5'-terminal of an oligonucleotide with the biotin can be given. The method of modification, however, is not limited to these methods and various other methods can be used. It is also possible to modify the 3'-terminal of an oligonucleotide with biotins.

The magnetic particles for bonding biotins and probe-bound particles of this embodiment can be suitably used for a biochip using particles, for example, the biochip disclosed in JP-A-2005-148048.

3. Examples

The present invention will now be described in more detail by way of examples, which should not be construed as limiting the present invention. In the examples, "%" is indicated on a weight basis.

3.1. Evaluation Method 3.1.1. Signal Measurement by CLEIA (Chemiluminescence Enzyme Immunity Assay)

10 microliters of a dispersion of probe-bonded particles (equivalent to 50 micrograms of particles) obtained in the later-described Examples and Comparative Examples was added to a test tube and mixed with 50 microliters of a standard sample of an AFP (alpha-fetoprotein) antigen (manufactured by NIPPON BIOTEST LABO.) diluted to a concentration of 100 ng/ml with fetal calf serum (FCS). The mixture was reacted at 37° C. for 10 minutes. After magnetically separating the particles and removing the supernatant liquid, 40 microliters of an anti-AFP antibody (a reagent attached to "Lumipulse AFP-N" manufactured by Fujirebio Inc.), labeled with an alkali phosphatase (ALP) as a secondary antibody, was added, followed by a reaction at 37° C. for 10 minutes. Next, after magnetic separation and removal of the supernatant liquid, the resulting particles were washed three times with PBS and dispersed in 50 microliter of 0.01% Tween 20. The resulting dispersion was transferred to a new tube. After the addition of 100 microliters of an ALP substrate solution (Lumipulse substrate solution manufactured by Fujirebio Inc.), the mixture was reacted at 37° C. for 10 minutes to measure the amount of chemiluminescence as a signal. A chemiluminescence luminometer ("Lumat LB9507" manufactured by Berthold Japan, Co., Ltd.) was used for measurement.

3.1.2. Measurement of Noise

The amount of chemiluminescence as noise was measured in the same manner as the signal measurement by CLEIA (chemiluminescence enzyme immunity assay) in 3.1.1. above, except that the dispersion of probe-bonded particles was not mixed with the standard sample.

3.1.3. Particle Size

The number average particle diameter of the particles and the coefficient of variation were measured using a laser diffraction particle size distribution analyzer ("SALD-200V" manufactured by Shimadzu Corp.).

3.1.4. Measurement of the Amount of Tosyl Groups Introduced Onto the Surface To determine the amount of tosyl groups on the surface of the magnetic particles, 100 mg of tosylated particles were washed three times with 1 ml of purified water and rotationally stirred in 1 ml of 1.0 M ethanolamine for 24 hours to dissociate p-toluenesulfonic acid from the particle surface. Then, the amount of tosyl groups was determined by measuring absorbance at 261 nm (epsilon=331).

3.1.5. Measurement of the Amount of Carboxyl Groups Introduced Onto the Surface The amount of carboxyl groups on the surface of the magnetic particles was measured by conductimetry (Metrohm Ltd., 794 Basic Titrino).

3.1.6. Measurement of Signal by PCR 1.0 mg of probe-bonded particles obtained in the later-described Examples and Comparative Examples were added to a test tube and dispersed in a 50 microliter of a dispersion liquid (5 mM Tris-HCl (pH 7.4)/1.0M NaCl/0.5 mM EDTA/ 0.05% Tween20). A biotinized oligonucleotide Biotin-p BR322 (100 mer) (prepared by PCR to have a 100 mer chain length using a primer of which one of the two primers' 5'-terminal was biotinized using pBR322 manufactured by Takara Bio Inc. as a template), equivalent to $1.0 \times 10^{15}$, was added to the tube, followed by stirring at 25° C. for one hour. Excess oligonucleotide was removed using a washing solution (25 mM Tris-HCl (pH 7.2)/1.0M NaCl/0.05% Tween 20). After washing, the particles were dispersed in 100 microliter of a 5 mM Tris-HCl buffer solution (pH 7.2) (containing 0.01% Tween 20). 10 microliter of the dispersion (0.01 mg) was used for determination of the bonded amount (signal) of Biotin-pBR322 (100) by real-time PCR method using a non-biotinized primer having the same sequence as the above primer. Real-time PCR by a TaqManProbe method was relied upon for detection. An ABI PRISM 7700 System (manufactured by Applied Biosystems Ltd.) was used in PCR.

3.1.7. Measurement of Noise by PCR

The amount of non-specific adsorption to the particles of oligonucleotide (noise) was determined in the same manner as in 3.1.4., except for using non-biotinized oligonucleotide pBR322 (100 mer).

3.2. Synthesis Example 1

2 parts by mass of 75% di(3,5,5-trimethylhexanoyl) peroxide solution ("Peroyl 355-75(S)" manufactured by NOF Corp.) and 20 parts by mass of 1% aqueous solution of sodium dodecylsulfate were mixed and finely emulsified using an ultrasonic dispersion machine. The emulsion was added to a reactor containing 13 parts by mass of polystyrene particles with a particle diameter of 0.77 micrometers and 41 parts by mass of water and the mixture was stirred at 25° C. for 12 hours. In another vessel, 96 parts by mass of styrene and 4 parts by mass of divinylbenzene were emulsified in 400 parts by mass of a 0.1% aqueous solution of sodium dodecylsulfate. The resulting emulsion was added to the above reactor. After stirring at 40° C. for two hours, the mixture was heated to 75° C. and polymerized for 8 hours. After cooling to room temperature, particles were separated by centrifugation, washed with water, dried, and ground to obtain non-magnetic nuclear particles (i) (formation of non-magnetic nuclear particles). The number average particle diameter of the non-magnetic nuclear particles (i) was 1.5 micrometers.

Next, ferrite-type fine magnetic material particles (average primary particle diameter: 0.01 micrometers) with a hydrophobized surface were prepared by adding acetone to an oily magnetic fluid ("EXP series" manufactured by Ferrotec Corp.) to obtain a precipitate of the particles and the precipitate was dried.

Then, 15 g of the above non-magnetic nuclear particle (i) and 15 g of the above magnetic material particles were thoroughly mixed in a mixer. The mixture was processed by a hybridization system ("Type NHS-0" manufactured by Nara Machinery Co., Ltd.) at a peripheral speed of blades (stirring blades) of 100 n/sec (16,200 rpm) for 5 minutes to obtain mother particles with a number average particle diameter of 2.0 micrometers, having a magnetic material layer of fine magnetic material particles on the surface.

Next, a 1 liter separable flask was charged with 375 g of an aqueous solution (hereinafter referred to as "aqueous solution of dispersion agent") of 0.25 wt % of sodium dodecylbenzenesulfonate and 0.25 wt % of a nonionic emulsifying agent ("Emulgen 150" manufactured by Kao Corp.), followed by the addition of 15 g of the mother particles having a magnetic material layer prepared above. The mother particles were dispersed using a homogenizer and heated to 60° C. A pre-emulsion, prepared by dispersing 27 g of methyl methacrylate, 3 g of trimethylolpropane trimethacrylate (TMP), and 0.6 g of di(3,5,5-trimethylhexanoyl) peroxide ("Peroyl 355" manufactured by NOF Corp.) in 150 g of the aqueous solution of dispersion agent, was added by drops to the above 1 liter separable flask controlled at 60° C. over one and half hours. After the addition, the mixture was stirred for one hour, while maintaining the temperature at 60° C. (formation of first polymer layer). A pre-emulsion, prepared by dispersing 13.5 g of glycidyl methacrylate (GMA), 1.5 g of TMP, and 0.3 g of di(3,5,5-trimethylhexanoyl) peroxide ("Peroyl 355" manufactured by NOF Corp.) in 75 g of the aqueous solution of dispersion agent, was added by drops to the above 1 liter separable flask controlled at 60° C. over one and half hours. After heating to 75° C., the polymerization was continued for two hours before completing the reaction (formation of second polymer layer). Subsequently, 60 ml of 1 mol/l sulfuric acid was added to the 1 liter separable flask and the mixture was stirred at 60° C. for six hours. The particles in the separable flask were magnetically separated and repeatedly washed with distilled water. Magnetic particles having a 2,3-dihydroxypropyl group (hereinafter indicated as "A-1 particles") were obtained in this manner. The amount of tosyl groups and the amount of carboxyl groups were 0 micromol/g (not present).

Next, 1.0 g of dry particles obtained by freeze drying the A-1 particles were dispersed in 8 ml of pyridine and 0.2 g of p-tosyl chloride was added. The mixture was stirred at room temperature for two hours. After the reaction, particles were magnetically separated and washed four times with acetone and four times with distilled water to obtain magnetic particles having an active group obtained by tosylating a 2,3-dihydroxypropyl group (hereinafter indicated as "B-1 particles") (introduction of tosyl group into second polymer layer). The number average particle diameter of the magnetic particles (B-1 particles) was 2.9 micrometers. The amount of tosyl groups was 70 micromol/g.

3.3. Synthesis Example 2

1.0 g of dry particles obtained by freeze-drying the A-1 particles of Synthesis Example 1 was dispersed in 9 ml of pyridine, 1 g of succinic anhydride was added, and the mixture was stirred at room temperature for two hours. After the reaction, particles were magnetically separated and washed four times with acetone and four times with distilled water to obtain magnetic particles having a 2,3-dihydroxypropyl group and a carboxyl group (a carboxyethylcarbonyloxy group) (hereinafter indicated as "B-2 particles") (introduction of carboxyethylcarbonyloxy group into second polymer layer). The number average particle diameter of the magnetic particles (B-2 particles) was 2.9 micrometers. The amount of carboxyl groups was 11 micromol/g.

3.4. Synthesis Example 3

1.0 g of dry particles obtained by freeze-drying the A-1 particles of Synthesis Example 1 was dispersed in 9 ml of pyridine, 1 g of glutaric anhydride was added, and the mixture was stirred at room temperature for two hours. After the reaction, particles were magnetically separated and washed four times with acetone and four times with distilled water to obtain magnetic particles having a 2,3-dihydroxypropyl group and a carboxyl group (a carboxypropylcarbonyloxy group) (hereinafter indicated as "B-3 particles") (introduction of carboxypropylcarbonyloxy group into second polymer layer). The number average particle diameter of the resulting magnetic particles (B-3 particles) was 2.9 micrometers. The amount of carboxyl groups was 8 micromol/g.

3.5. Comparative Synthesis Example 1

Magnetic particles having a carboxyl group, but not having a 2,3-dihydroxypropyl group (hereinafter indicated as "B-4 particles") were obtained in the same manner as Synthesis Example 1 except for using 13 g of cyclohexylmethacrylate and 1.5 g of methacrylic acid instead of 13.5 g of GMA and 1.5 g of TMP. The number average particle diameter of the resulting magnetic particles (B-3 particles) was 2.9 micrometers.

3.6. Example 1

10 mg of B-1 particles were dispersed in a boric acid buffer solution (pH 9.5) and 0.1 ml of a solution of 1 mg of streptavidin (manufactured by Sigma-Aldrich Co.) was added to the buffer solution. After rotationally stirring at 37° C. for 16 hours, the particles were washed three times with a Tris buffer solution, thereby obtaining biotin-bonded particles with streptavidin immobilized on the surface. 1 mg of the biotin-bonding particles were dispersed in a PBS/0.01% Tween 20 solution and 10 microgram of a biotinization anti-AFP antibody was added, followed by reaction at room temperature for one hour. The particles were washed three times with the PBS/0.01% Tween 20 solution to obtain probe-bonded particles with an anti-AFP antibody bonded. The signal of the probe-bonded particles of Example 1 was 170,940 and the noise was 150. The signal of the resulting probe-bonded particles determined by the PCR method was $3.0 \times 10^{13}$/mg and the noise was $1.3 \times 10^5$/mg.

3.7. Example 2

0.1 ml of a 0.1 mM HCl solution in which 5 mg of 1-ethyl-3-dimethylaminopropylcarbodiimide hydrochloride (manufactured by Dojindo Laboratories) was dissolved was added to 1 ml of an aqueous dispersion of the B-2 particles with a solid content of 1% and the mixture was rotationally stirred at room temperature for two hours. 0.1 ml of a 0.1 mM HCl solution in which 1 mg of streptavidin (manufactured by Sigma-Aldrich Co.) was dissolved was added, followed by rotational stirring at room temperature for eight hours. Next, the particles were magnetically separated by repeating a procedure of adding a phosphate buffer solution (PBS, 0.1% BSA/PBS, pH=7.2) containing 0.1% bovine serum albumin three times and unreacted streptavidin was removed to obtain particles for bonding biotins with streptavidin immobilized on the surface. 1 mg of the biotin-bonding particles were dispersed in a PBS/0.01% Tween 20 solution and 10 microgram of a biotinization anti-AFP antibody was added, followed by reaction at room temperature for one hour. The particles were washed three times with the PBS/0.01% Tween 20 solution to obtain probe-bonded particles of Example 2 with an anti-AFP antibody bonded. The signal of the probe-bonded particles of Example 2 was 157,582 and the noise was 70. The signal of the resulting probe-bonding particles determined by the PCR method was $3.0 \times 10^{13}$/mg and the noise was $1.1 \times 10^5$/mg.

3.8. Example 3

Probe-bonded particles of Example 2 with an anti-AFP antibody bonded were obtained in the same manner as in Example 2, except for using B-3 particles. The signal of the probe-bonding particles of Example 2 was 148,561 and the noise was 120. The signal of the resulting probe-bonding particles determined by the PCR method was $2.5 \times 10^{13}$/mg and the noise was $2.0 \times 10^5$/mg.

3.9. Comparative Example 1

Probe-bonded particles of Comparative Example 1, which are outside of the scope of the invention, were obtained in the same manner as Example 2 except for using the B-4 particles. The signal of the probe-bonded particles of the Comparative Example 1 determined by the CLEIA method was 36,059 and the noise was 306. The signal of the resulting probe-bonded particles by the PCR method was $5.0 \times 10^{12}$/mg and the noise was $2.6 \times 10^6$/mg. Based on these results, the probe-bonded particles of Comparative Example 1 were confirmed to exhibit a lower signal and a greater noise as determined in CLEIA and PCR as compared with the probe-bonded particles of Examples 1, 2, and 3. Thus, it can be understood that a substance having a biotin-bonding site can be immobilized on the probe-bonded particles of Examples 1, 2, and 3 by introducing a group shown by the above formula (2) or formula (3) into magnetic particles having a 2,3-dihydroxypropyl group and reacting the substance having a biotin-bonding site with the group shown by the above formula (2) or formula (3), whereby the probe-bonded particles of Examples 1, 2, and 3 can exhibit high sensitivity and low noise.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

What is claimed is:

1. Magnetic particles, each comprising
a non-magnetic material nucleus;
a magnetic material layer on the non-magnetic material nucleus; and
an organic polymer layer on the magnetic material layer, wherein
the organic polymer layer comprises an organic polymer comprising a group shown by the following formula (1) and a 2,3-dihydroxypropyl group,

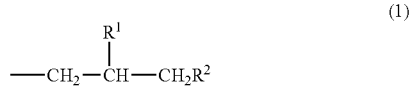

wherein $R^1$ and $R^2$ individually represent a hydroxyl group, a group shown by the following formula (2), or a group shown by the following formula (3), provided that $R^1$ and $R^2$ are not both hydroxyl groups,

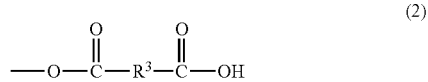

wherein $R^3$ represents an a linear, branched, or cyclic alkylene group having 2 to 6 carbon atoms or an arylene group, and

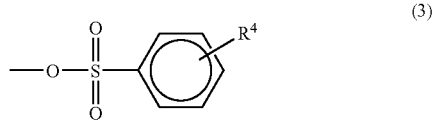

wherein $R^4$ is a hydrogen atom or an alkyl group.

2. The magnetic particles as defined in claim 1, wherein the organic polymer further comprises an epoxy group.

3. The magnetic particles as defined in claim 1, wherein the organic polymer layer comprises a first organic polymer layer and a second organic polymer layer which covers the first organic polymer layer; and the second polymer layer comprises the group shown by the formula (1).

4. The magnetic particles as defined in claim 3, wherein the second polymer layer further comprises the 2,3-dihydroxypropyl group.

5. The magnetic particles as defined in claim 3, wherein the second polymer layer further comprises an epoxy group.

6. The magnetic particles as defined in claim 5, wherein each of the magnetic particles has a biotin-bonded probe bonded to the organic polymer layer.

7. The magnetic particles as defined in claim 1, wherein each of the magnetic particles has a substance having a biotin-bonding site immobilized on the organic polymer layer.

8. The magnetic particles as defined in claim 7, wherein the substance having a biotin-bonding site is at least one compound selected from the group consisting of avidin, streptavidin, and their derivatives.

9. The magnetic particles as defined in claim 1, wherein the magnetic material layer comprises superparamagnetic particles.

10. The magnetic particles as defined in claim 1, wherein the magnetic material layer comprises iron oxide particles.

11. A method of using magnetic particles, the method comprising
providing the magnetic particles of claim 1, where at least one of R1 and R2 of the organic polymer comprises the group shown by the formula (2); and
reacting a substance having a biotin-bonding site with the group shown by the formula (2).

12. The method as defined in claim 11, wherein
the magnetic particles further comprise an epoxy group; and
the method further comprises reacting the substance having a biotin-bonding site with the epoxy group.

13. A method of using magnetic particles, the method comprising
providing the magnetic particles of claim 1, where at least one of R1 and R2 of the organic polymer comprises the group shown by the formula (3); and
reacting a substance having a biotin-bonding site with the group shown by the formula (3).

14. The method as defined in claim 13, wherein
the magnetic particles further comprise an epoxy group; and
the method further comprises reacting the substance having a biotin-bonding site with the epoxy group.

* * * * *